US006434488B1

(12) United States Patent
Robson

(10) Patent No.: US 6,434,488 B1
(45) Date of Patent: Aug. 13, 2002

(54) ALIGNMENT FREE METHODOLOGY FOR RAPID DETERMINATION OF DIFFERENCES BETWEEN A TEST DATA SET AND KNOWN DATA SETS

(75) Inventor: Barry Robson, Bronxville, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/454,379

(22) Filed: Dec. 3, 1999

(51) Int. Cl.[7] ........................... G01N 33/48; G06F 17/14
(52) U.S. Cl. ............................... 702/19; 702/20; 708/3; 708/5; 708/203; 708/210; 708/230; 708/400; 712/36
(58) Field of Search ........................ 702/19, 20; 708/3, 708/5, 203, 210, 230, 400; 712/36

(56) References Cited

U.S. PATENT DOCUMENTS 5,511,159 A * 4/1996 Baker et al. ................. 395/161
6,236,958 B1 * 5/2001 Lange et al. .................... 704/8

OTHER PUBLICATIONS

G. Stolovitzky et al., "Statistical Significance of Patterns in Biosequences," IBM Computational Biology Center, Yorktown Heights, New York, pp. 1–14, Oct. 9, 1998.

I. Rigoutsos et al., "Motif Discovery Without Alignment or Enumeration," Proceedings 2nd Annual ACM International Conference on Computational Molecular Biology (RECOMB '98), New York, New York, pp. 1–7, Mar. 1998.

I. Rigoutsos et al., "Combinatorial Pattern Discovery in Biological Sequences: The TEIRESIAS Algorithm," Bioinformatics, vol. 14, No. 1, Oxford University Press, pp. 55–67, 1998.

I. Rigoutsos et al., "IBM Research Report: Case Studies in Pattern Discovery Without Alignment Results Using the TEIRESIAS Algorithm," RC 20803 (92166), pp. 1–11, Apr. 21, 1997.

H.B. Nicholas Jr. et al., "A Tutorial on Searching Sequence Databases and Sequence Scoring Methods," Sequence Database Searching and Sequence Scoring Methods Tutorial, http://www.psc.edu/biomed/TUTORIAL/SEQUENCE/DB-SEARCH/tutorial.html, pp. 1–23, Jan. 1997 (Revised Mar. 1998).

S.F. Altschul et al., "Basic Local Alignment Search Tool," J. Mol. Biol., vol. 215, pp. 403–410, 1990.

W.R. Pearson et al., "Improved Tools for Biological Sequence Comparison," Proc. Natl. Acad. Sci. USA (Biochemistry), vol. 85, pp. 2444–2448, Apr. 1988.

S. French et al., "What is a Conservative Substitution?," Journal of Molecular Evolution, vol.19, pp. 171–175, Springer–Verlag, 1983.

E. Nagel et al., "Goedel's Proof," pp. 282–291, New York University Press, 1958.

T. Nagell, "Introduction to Number Theory," pp. 14–17, John Wiley & Sons, Inc., New York, 1951.

* cited by examiner

Primary Examiner—Mary K. Zeman
(74) Attorney, Agent, or Firm—Casey P. August; Ryan, Mason & Lewis, LLP

(57) ABSTRACT

A method for generating data characterizing an item described by an ordered string of characters, comprises the steps of: (i) for a set of separation metrics each representing a unique number of positions of separation between arbitrary characters in a character group in the ordered string of characters, associating first with each separation metric; generating a set of character groups, wherein each character group comprises at least two characters contained within the ordered string of characters; and (ii) for at least one given character group in the set of character groups, for each given separation metric in the set of separation metrics, generating second data representing number of occurrences that the given character group satisfies the given separation metric; generating third data associated with the given character group, wherein the third data is based upon the second data and the first data; and storing the third data in memory for subsequent use.

22 Claims, 14 Drawing Sheets

FIG. 3 EXAMPLE CODE FOR CREATING A FINGER ARRAY

```
atypes=20;
btypes=20;

for (locus = 1;locus=<sequence_length;locus++) {
       for (a=1;a=<atypes;a++) {
               for b=1;b=<btypes;b++) {
                       finger[a][b]=0;
                    }
         }

FOR (i=locus-1; i>0 & i>=locus-m; i - - ) {
                 finger[sequence[i-1];][sequence[locus]] += Λ(locus-i);
            }
}
``` where $\Lambda(j)$ for all j subject to $0\sim j=<k$, is precalculated at initialization time (see Method).

FIG. 4 EXAMPLE CODE FOR COMPARING A PROBE FINGER AND SEQUENCE FINGER ARRAY

```
score=0;
k=0;
FOR (a = 1;a=<atypes;a++) {
        FOR (b=1;b=<btypes;b++) {
                        f = finger[a][b];
                        p = probe [a][b];
                        score += ABS(f - p);
                        }
        }
score=score/total;

where total is pre-calculated at initialization time as
total = 0;
FOR (m=1; m=<k;i++) {
        total += Λ(m)
        }
total = total * 400
```

FIG. 5A INITIAL TEST DATA BASE OF PROTEINS OF KNOWN CONFORMATION AND WELL-DEFINED SECONDARY STRUCTURE

| | |
|---|---|
| TESTDB 330 | 6 4APE1E ACID PROTEINASE ENDOTHIAPEPSIN |
| TESTDB 323 | 6 2APE1E ACID PROTEINASE, PENICILLOPEPSIN [HYDROLASE: PROTEINASE] {F |
| TESTDB 218 | 6 2ACT1M ACTINIDIN [HYDROLASE: SULFHYDRYL PROTEINASE] {KIWIFRUIT: AC |
| TESTDB 170 | 6 3WGA1M LECTIN (AGGLUTININ) WHEAT GERM |
| TESTDB 374 | 6 4ADH1M APO-LIVER ALCOHOL DEHYDROGENASE [OXIDOREDUCTASE: CHOH/DONR, |
| TESTDB 198 | 6 2ALP1E ALPHA LYTIC PROTEASE [HYDROLASE:SERINE PROTEINASE] {MYXOBA |
| TESTDB 310 | 6 4ATC1M ASPARTATE TRANSCARBAMYLASE (E. COLI) CHAIN 1 |
| TESTDB 153 | 6 4ATC2M ASPARTATE TRANSCARBAMYLASE (E. COLI) CHAIN 2 |
| TESTDB 129 | 6 1AZA1E AZURIN ELECTRON TRANSPORT PROTEIN |
| TESTDB 74 | 6 2ABX1M BUNGAROTOXIN BRAIDED KRAIT VENOM |
| TESTDB 108 | 6 1CPV1H CALCIUM-BINDING PARVALBUMIN B [CALCIUM BINDING PROTEINS] {C |
| TESTDB 75 | 6 31CB1H CALCIUM BINDING PROTEIN BOVINE INTESTINEVIT. D DEPENDANT |
| TESTDB 256 | 6 2CAB1E CARBONIC ANHYDRASE FORM B HUMAN ERYTHROCYTES |
| TESTDB 307 | 6 5CPA1M CARBOXYPEPTIDASE A [C-TERMINAL AMINO ACID HYDROLASE] {COW P |
| TESTDB 498 | 6 8CAT1M CATALASE BEEF LIVER |
| TESTDB 131 | 6 5CHA1E ALPHA CHYMOTRYPSIN A (BOS TAURUS) CHAIN 1 |
| TESTDB 437 | 6 2CTS1H CITRATE SYNTHASE PIG HEART |
| TESTDB 46 | 6 1CRN1M CRAMBIN [PLANT SEED PROTEIN] {ABYSSINIAN CABBAGE SEED: CRAM |
| TESTDB 174 | 6 1GCR1E GAMMA -/11$ CRYSTALLIN CALF EYE LENS |
| TESTDB 103 | 6 3CYT1H CYTOCHROME C (OXIDIZED) [ELECTRON TRANSPORT] {ALBACORE TUNA |
| TESTDB 111 | 6 1CCR1M CYTOCHROME C RICE EMBRYOS |
| TESTDB 127 | 6 2CCY1H CYTOCHROME C PRIME (RHODOSPIRILLUM MOLISCHIANUM) |
| TESTDB 293 | 6 2CYP1H CYTOCHROME C PEROXIDASE (BAKER'S YEAST) |
| TESTDB 112 | 6 3C2C1H FERRICYTOCHROME C2 [ELECTRON TRANSPORT] {BACTERIAL: RHODOSP |
| TESTDB 107 | 6 2CDV1M CYTOCHROME C3 (DISULFOVIBRIO VULGARIS) |
| TESTDB 82 | 6 351C1H CYTOCHROME C551 (OXIDIZED) [ELECTRON TRANSPORT] {PSEUDOMONA |
| TESTDB 162 | 6 3DFR1M DIHYDROFOLATE REDUCTASE [OXIDOREDUCTASE: NADPH/DONR,DIHYDRO |
| TESTDB 240 | 6 2EST1E ELASTASE PORCINE PANCREAS |
| TESTDB 62 | 6 2EBX1E ERABUTOXIN SEA SNAKE VENOM |
| TESTDB 136 | 6 1ECD1H HEMOGLOBIN (ERYTHROCRUORIN,DEOXY) [OXYGEN TRANSPORT] {CHIR |
| TESTDB 54 | 6 1FDX1M FERREDOXIN [ELECTRON TRANSPORT] {PEPTOCOCCUS AEROGENES} .... |
| TESTDB 98 | 6 3FXC1M FERREDOXIN [ELECTRON TRANSPORT] {SPIRULINA PLATENSIS} ...... |
| TESTDB 138 | 6 3FXN1M FLAVODOXIN (OXIDIZED) [ELECTRON TRANSPORT] {CLOSTRIDIUMMP} |
| TESTDB 106 | 6 2FD11M FERREDOXIN AZOBACTER |
| TESTDB 184 | 6 1GP11M GLUTATHIONE REDUCTASE BOVINE ERYTHROCYTES |

FIG. 5B  INITIAL TEST DATA BASE (cont'd)

| | | |
|---|---|---|
| TESTDB 113 | 6 1HMQ1H | HEMERYTHRIN (MET) SIPUNCULID WORM |
| TESTDB 141 | 6 2HHB1H | HEMOGLOBIN (HUMAN,DEOXY) CHAIN1 |
| TESTDB 146 | 6 2HHB2H | HEMOGLOBIN (HUMAN,DEOXY) CHAIN2 |
| TESTDB 149 | 6 2LHB1H | HEMOGLOBIN V (CYANO,MET) SEA LAMPREY |
| TESTDB 85 | 6 1H1P1M | OXIDIZED HIGH POTENTIAL IRON PROTEIN (HIPIP) [ELECTRON TRAN |
| TESTDB 220 | 6 1MPC1E | IMMUNOGLOBULIN FAB IGG (MOUSE) CHAIN 1 |
| TESTDB 222 | 6 1MPC2E | IMMUNOGLOBULIN FAB IGG (MOUSE) CHAIN 2 |
| TESTDB 229 | 6 1FB42E | IMMUNOGLOBULIN FAB (HUMAN MYELOMA) CHAIN 2 |
| TESTDB 107 | 6 1RE11E | BENCE-JONES IMMUNOGLOBULIN VARIABLE PORTION (REI) {HUMAN}.. |
| TESTDB 114 | 6 2RHE1E | BENCE JONES PROTEIN LAMBDA VARIABLE DOMAIN (HUMAN) |
| TESTDB 80 | 6 2PKA1E | KALLIKREINA (PROCINE PANCREAS) CHAIN 1 |
| TESTDB 152 | 6 2PKA2M | KALLIKREINA (PORCINE PANCREAS) CHAIN 2 |
| TESTDB 329 | 6 4LDH1M | LACTATE DEHYDROGENASE, APO ENZYME M4 [OXIDOREDUCTASE: CHOH/ |
| TESTDB 153 | 6 1LH11H | LEGHEMOGLOBIN (ACETATE,MET) [OXYGEN TRANSPORT] {YELLOW LUPI |
| TESTDB 164 | 6 2LZM1M | LYSOZYME (BACTERIOPHAGE T4) |
| TESTDB 130 | 6 1LZ11M | LYSOZYME (HUMAN) |
| TESTDB 153 | 6 1MBN1M | MYOGLOBIN [OXYGEN STORAGE] (FERRIC IRON - METMYOGLOBIN) {SP |
| TESTDB 26 | 6 1MLT1H | MELITTIN [HEMOLYTIC POLYPEPTIDE] {HONEY BEE VENOM: APIS MEL |
| TESTDB 62 | 6 1NXB1E | NEUROTOXIN B (PROBABLY = ERABUTOXIN B) {SEA SNAKE: LATICAUD |
| TESTDB 65 | 6 1SN31M | SCORPION NEUROTOXIN |
| TESTDB 56 | 6 1OVO1M | OVOMUCOID THIRD DOMAIN [PROTEINASE INHIBITOR,KAZAL] {JAPAN |
| TESTDB 212 | 6 1PPD1M | PAPAIN SULFHYDRYL PROTEINASE (PAPAYA FRUIT LATEX) |
| TESTDB 123 | 6 1BP21M | PHOSPHOLIPASE A2 [PHOSPHATIDE ACYL-HYDROLASE] {COW PANCREAS |
| TESTDB 99 | 6 1PCY1E | PLASTOCYANIN [ELECTRON TRANSPORT, COPPER BINDING] {POPLAR L |
| TESTDB 114 | 6 2PAB1E | PREALBUMIN [THYROXIN, RETINOL TRANSPORT] {HUMAN PLASMA}.... |
| TESTDB 181 | 6 2SGA1E | PROTEINASE A (SGPA) [HYDROLASE: SERINE PROTEINASE] {STREPTO |
| TESTDB 224 | 6 3RP21E | SERINE PROTEINASE (RAT MAST CELL PROTEASE) |
| TESTDB 124 | 6 1RN31M | RIBONUCLEASE A (BOVINE PANCREAS) |
| TESTDB 54 | 6 4RXN1M | RUBREDOXIN IRON-SULFUR PROTEIN (CLOSTRIDIUM) |
| TESTDB 141 | 6 2SNS1M | STAPHYLOCOCCAL NUCLEASE |
| TESTDB 275 | 6 1SBT1M | SUBTILISIN BPN' [HYDROLASE: SERINE PROTEINASE] {PROBABLY BA |
| TESTDB 151 | 6 2SOD1E | CU,ZN SUPEROXIDE DISMUTASE [OXIDOREDUCTASE: SUPEROXIDE/ACCP |
| TESTDB 316 | 6 3TLN1M | THERMOLYSIN [HYDROLASE: NEUTRAL METALLO-PROTEINASE] {BACILL |
| TESTDB 223 | 6 1TPO1E | BETA TRYPSIN (BOVINE) ORTHOROMBIC |
| TESTDB 58 | 6 4PT11M | TRYPSIN INHIBITOR [PROTEINASE INHIBITOR] {COW PANCREAS: BOS |
| TESTDB 184 | 6 2STV1E | COAT PROTEIN OF SATELLITE TABACCO NECROSIS VIRUS |
| TESTDB 222 | 6 4SBV1E | SOUTHERN BEAN MOSAIC VIRUS COAT PROTEIN |

FIG. 6

|   | W | F | Y | M | L | I | V | C | A | P | G | T | S | Q | N | D | E | H | K | R |
|---|---|---|---|---|---|---|---|---|---|---|---|---|---|---|---|---|---|---|---|---|
| W |   |   |   |   |   |   |   |   |   |   |   |   |   |   |   |   |   |   | 2 | 3 |
| F |   |   |   |   |   |   |   |   |   |   |   | 4 |   |   |   |   |   |   | 2 | 3 |
| Y |   |   |   |   |   |   |   |   |   |   |   |   |   |   | 1 |   | 1 |   | 2 | 3 |
| M |   |   | 3,4 |   |   |   |   |   | 1,3 | 1 |   |   |   |   | 1 | 2 |   |   | 2 | 3 |
| L |   |   |   |   |   |   |   |   |   |   |   |   |   |   |   |   |   |   | 2 | 3 |
| I |   |   |   |   |   |   | 1,2 |   |   |   |   |   |   |   |   |   |   |   |   |   |
| V |   |   |   |   |   |   |   |   |   |   |   | 1,4 | 5 |   | 1 |   |   |   |   | 2 |
| C |   |   |   |   |   |   |   |   |   |   |   |   |   |   |   |   |   | 1 |   |   |
| A | 1 | 1 | 1 | 1 | 1 | 2 | 2 |   |   | 1,4 | 1 |   |   | 1 |   |   |   |   |   | 3 |
| P |   |   |   | 2 |   |   |   |   |   |   |   |   | 3 |   |   |   | 1 | 5 |   |   |
| G |   |   |   |   |   |   | 1 |   | 1 |   |   |   |   |   |   |   |   |   |   |   |
| T |   |   |   |   |   |   |   |   |   |   |   |   |   |   |   |   |   |   | 5 | 3 |
| S |   |   |   |   | 1 |   |   |   | 1,4 |   |   | 2,4 | 2,4 | 1 |   |   |   |   | 5 | 3 |
| Q |   |   |   |   |   |   |   |   |   |   |   |   |   |   |   | 4 |   |   |   | 3 |
| N |   |   |   | 2 |   |   |   |   |   |   |   | 2 |   | 2 |   |   |   |   |   | 3 |
| D |   |   |   |   |   |   |   |   |   |   |   | 3 |   |   |   |   |   |   | 3 | 4 |
| E | 1,2 | 1,2 | 1,2 | 1,2 | 1,2 |   |   |   |   |   |   |   |   |   |   | 3,4 |   |   |   |   |
| H |   |   |   |   |   |   |   |   |   |   |   | 3 |   |   |   |   |   |   |   |   |
| K |   |   | 2 |   |   |   |   |   | 3 | 3 |   |   |   |   |   | 3,4 |   | 1,2 |   |   |
| R |   |   |   |   |   |   |   |   | 1 |   |   | 3 |   |   |   |   |   |   |   |   |

| HELIX |
|---|
| SHEET |
| LOOP |

| SIMILAR HELIX (3-4) AND SHEET / (1-2) PROPENSITY |
|---|

FIG. 7

| | LINEAR: GRAD & CONST | FMAX SONIC (1) | VS. % HOMOLOGY =(1-P_{F=Fmax}/2)*100 |
|---|---|---|---|
| BEST FIT CURVE TO PRIMARY STRUCTURE | 0.65 (~0) | 0.9 | 70% |
| PRIMARY STRUCTURE UPPER 90% OF RANDOMIZED SEQUENCES | 1 (+0.13) | 0.95 | 80% |
| PRIMARY STRUCTURE LOWER 90% OF RANDOMIZED SEQUENCES | 0.55 (0) | 0.85 | 60% |
| PRIMARY STRUCTURE: UPPER 90% OF REAL REPORTED NON-HOMOLOGOUS SEQUENCES | 0.75 (+0.26) | 0.95 | 80% |
| PRIMARY STRUCTURE LOWER 90% OF REAL REPORTED NON-HOMOLOGOUS SEQUENCES | 0.5 (~0) | 0.65 | 70% |

FIG. 8

| FINGER INDEX | QUALITATIVE SIGNIFICANCE SONIC(1) | QUALITATIVE SIGNIFICANCE PRIMAL |
|---|---|---|
| 0.95-1.0 | WORSE THAN RANDOM | NO RELATIONSHIP (worse than random) |
| 0.65-0.85 | 0%-60% HOMOLOGY | 0%-20% HOMOLOGY |
| 0.35-0.45 | 55%-87% HOMOLOGY | 20%-65% HOMOLOGY |
| 0.25-0.35 | 70%-93% HOMOLOGY | 40%-80% HOMOLOGY |
| 0.0-0.15 | 90%-100% HOMOLOGY | 80%-100% HOMOLOGY |
| HOMOLOGY OF 50% BETWEEN REAL PROTEIN SEQUENCES | FINGER INDEX 0.5-0.75 | FINGER INDEX 0.3-0.43 |
| IMPLICATION FROM FINGER INDEX FOR 50% HOMOLOGY | PREDICTED HOMOLOGY 30% ± 30% | PREDICTED HOMOLOGY 50% ± 10% |

FIG. 9 EFFECT OF ALTERING ORDER OF SEGMENTS OF SEQUENCE

| | PREVIOUS f | f AFTER "MIXING" |
|---|---|---|
| UNCHANGED | f = 0.000 | f = 0.000 |
| REVERSE ORDER OF 160 RESIDUE SEGMENTS | f = 0.000 | f = 0.032 |
| REVERSE ORDER OF 80 RESIDUE SEGMENTS | f = 0.000 | f = 0.053 |
| REVERSE ORDER OF 20 RESIDUE | f = 0.000 | f = 0.148 |
| REVERSE ORDER OF 20 RESIDUE SEGMENTS, COMPARE WITH 50% HOMOLOGOUS SEQUENCES | <f> = 0.366 | <f> = 0.384 |
| REVERSE ORDER OF 20 RESIDUE SEQUENCES, COMPARE WITH 15-25% HOMOLOGY AND COMMON FOLD | <f> = 0.559 | <f> = 0.575 |

FIG. 12A

| SEPARATION IN X FORMAT = | | X | XX | XXX |
|---|---|---|---|---|
| SEPARATION = | 1 | 2 | 3 | 4 |
| RS | OCCURRENCES = | 1 | 0 | 0 | 0 |
| RR | | 2 | 2 | 1 | 1 |
| SS | | 0 | 0 | 0 | 0 |
| SR | | 1 | 1 | 1 | 0 |

FIG. 12B

| | SEPARATION = | 1 | 2 | 3 | 4 |
|---|---|---|---|---|---|
| RS | OCCURRENCES = | log2 | 0 | 0 | 0 |
| RR | | 2log2 | 2log3 | log5 | log7 |
| SS | | 0 | 0 | 0 | 0 |
| SR | | log2 | log3 | log5 | 0 |

FIG. 12C

|   | R | S |
|---|---|---|
| R | 2log2 + 2log3 + log5 + log7 | log2 |
| S | log2 + log3 + log5 | |

ALIGNMENT FREE METHODOLOGY FOR RAPID DETERMINATION OF DIFFERENCES BETWEEN A TEST DATA SET AND KNOWN DATA SETS

FIELD OF THE INVENTION

The present invention generally relates to data comparison methodologies and, more particularly, to methods and apparatus for performing an alignment free and rapid determination of differences between a test data set, e.g., a probe protein sequence, and known data sets, e.g., a given protein sequence data base.

BACKGROUND OF THE INVENTION

It is known that there are various deficiencies in existing methods associated with certain applications in bioinformatics and computational genomics. These deficiencies are of increasing concern as the level of genomic data mounts. Of particular concern are existing algorithms designed to detect similar protein sequences in a known database given a test sequence. For example, many of such existing algorithms implicitly or explicitly require a sequence alignment operation despite the fact that it is desirable to avoid such an operation. Further, none of the existing algorithms are particularly well suited for efficient utilization on a relational data base. Still further, current protein sequence search and sequence-pattern recognition methods depend on very sophisticated mathematical methodologies.

Examples of such existing methodologies include Smith-Waterman (M. S. Waterman, "Introduction to Computational Biology," Chapman & Hall, London (Smith-Waterman), 1988), BLAST (S. F. Altschul, W. Gish, W. Miller, E. W. Myers and D. J. Lipman, J. Mol. Biol., 215, 403–410 (BLAST), 1990), FASTA (W. R. Pearson and D. J. Lipman, Proc. Nat. Acad. Sci.uS, 85, 2444–2448 (FASTA), 1988). While the above methodologies are approaches inherently based on, and aiding, protein sequence alignment in order to abstract common features, more recent approaches such as TERESIAS and SPLASH eschew the need for alignment by directly abstracting common patterns, see, e.g., I. Rigoustos, A. Floratos, and C. Ouzounis, IBM RC20803(92166), Apr. 26, 1976; A. Califano and I. Rigoustos, In Proc. Symp. on Intelligent Systems for Mol. Biol., Washington; G. Stolovitsky and A. Califano, "Discrete Applied Mathematics Series," ed. P. Penver; and I. Rigoustos and A. Floratos, In Proc. 2nd Annual ACM Intnl. Conf. of Comp. Mol. Biol., 1993. By assembling directories of patterns in known protein sequences and pointers to their source proteins, the latter three approaches can also be used to sensitively identify protein sequences which are related. However, these latter approaches require the derivation, continued updating and use of large dictionaries of patterns or "motifs." Also, none of the approaches are especially well suited to relational databases.

SUMMARY OF THE INVENTION

The present invention provides methods and apparatus for performing an alignment free and rapid determination of differences between a test data set and known data sets. In a broad aspect of the invention, a method for generating data characterizing an item described by an ordered string of characters, comprises the steps of: (i) for a set of separation metrics each representing a unique number of positions of separation between arbitrary characters in a character group in the ordered string of characters, associating first with each separation metric; generating a set of character groups, wherein each character group comprises at least two characters contained within the ordered string of characters; and (ii) for at least one given character group in the set of character groups, for each given separation metric in the set of separation metrics, generating second data representing number of occurrences that the given character group satisfies the given separation metric; generating third data associated with the given character group, wherein the third data is based upon the second data and the first data; and storing the third data in memory for subsequent use.

Preferably, said item is a protein sequence, and each character in the ordered string of characters represents at least one amino acid. Further, each character group may comprise a character pair contained within the ordered string of characters, and wherein each separation metric represents a unique number of positions of separation between arbitrary characters in a character pair in the ordered string of characters. The third data may be stored in an entry associated with the given character pair, wherein the entry is part of table of entries stored in memory, wherein each entry corresponds to a unique character pair. The first data may comprise a set of unique prime numbers corresponding to set of separation metrics. The set of unique prime numbers may be an ordered set beginning with the number 2. The step of generating the third data associated with the given character pair may be generated by: for each given separation metric in the set of separation metrics, transforming the second data using a function based upon the unique prime number associated with the given separation metric; and adding the transformed first data to a running sum associated with the given character pair. The transforming step may comprise multiplying the second data by the natural logarithm of the unique prime number associated with the given separation metric.

Further, the method may provide that the table entries for a given item be compared with the table entries for another item to provide a measure of similarity between the two items. The comparison between table entries for the two items is preferably based upon the numerical difference between corresponding table entries. Still further, the measure of similarity between the two items is preferably computed by: summing the absolute value of the numerical difference between corresponding table entries, and normalizing the resultant sum.

In a specific embodiment in the context of genetic information processing, the present invention provides a methodology of representing protein sequences or parts thereof by a "fingerprint" or "recognition silhouette" which identifies a protein as belonging to a particular class. To achieve this, the present invention enables rapid estimation of degrees of relatedness in a form of "pattern content" sense, which also has more specific routine applications. The particular significance is that a data base searched can consist of fingerprints representing whole sequences or parts of sequences (including segments of sequences sometimes called "blocks," domains" or "sub-domains," and such fingerprints may serve as an alternative to storage of specific sequence, or can represent whole families, or recreate parts of proteins such as domains or even relatively small fragments and consensus sequences.

To do this, pattern matching and its application in genomics to searching for homologousprotein sequences, is expressed in some of the concepts of prime number theory. In accordance with the invention, patterns can be seen as recurrent prime factors which one may deem irreducible in string data, or relatively prime in the context of the problem addressed, and their isolation from the embedding string data corresponds to factorization. Though this may be simple analogy rather than a "deep relationship," comparison leads to some useful preliminary screening tools for showing the relationships between two sequences of symbols.

To do this, patterns in a special representational form are identified. This special representational form is referred to as a "finger matrix." A simple mapping by pattern data to prime numbers is defined, and is used, in turn, to encode multiple symbol-separation data into the simple scalar elements of a 20×20 residue (amino acid type) array, in one embodiment, this matrix being characteristic of individual protein sequences (assuming a sliding window of 10 residues).

Generally, a homology refers to a similarity, likeness, or relation between two or more sequences or strings. However, as will be explained, the invention provides homology detection through a methodology of identifying differences between a given sample and a known data base. In a specific application, the method is employed to measure the differences between sequences, rather than looking for common features, and thus is very different from other methods, especially TEIRESIAS and SPLASH, and with a different purpose. This is because the invention was also in part developed to obtain estimates of the effort required (or "scope of problem") in modeling a protein from a homologue of known conformation. To that end, the difference between the finger matrix (as the pattern representational form) is measured, such that the points of sequence difference are counted. While that aspect of emphasizing differences must be born in mind, implying a non-classical kind of homology metric, the matrices have utility as a finger matrix or "fingerprint" characteristic of specified protein sequences, and the difference matrix for two specified sequences is a measure of percent homology by classical definition. This relation with classical measure holds when homology is distributed throughout the length though not necessarily between segments in the same order, and it is not affected by insertions or deletions with one sequence with respect to the other. Importantly, therefore, alignment is not required. The finger matrices optionally can be calculated in advance for a protein sequence data bank, allowing very high speed matching and screening prior to more diligent analyses. The nature of the finger matrix also lends itself readily to treatment of sets, including fuzzy sets, of amino acid types, and definitions of sets can be introduced at the time of comparing or subtracting finger matrices.

It is to be appreciated that the methodologies of the invention may be employed in various other applications. For example, the present invention finds application in determining relationships associated with deoxyribonucleic acid (DNA) and ribonucleic acid (RNA). More generally, the invention may be used in any situation involving a series of text or symbols, or data which may be converted to text or symbols, in order to look for relationships associated therewith. By way of example only, data may be processed in accordance with the present invention which represents peaks in graphs, features such as mountain ranges, and fluctuations in the stock exchange. Given the inventive teachings provided herein, one of ordinary skill in the art will realize other and varied applications of the invention.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 3 is an example of software code for generating a finger matrix according to one embodiment of the present invention;

FIG. 4 is an example of software code for comparing a probe finger matrix and a sequence finger matrix according to one embodiment of the present invention;

FIG. 5A illustrates an initial test data base of proteins for use in accordance with a sequence conversion and finger matrix comparison system according to one embodiment of the present invention;

FIG. 5B illustrates a continuation of the initial test data base illustrated in FIG. 5A;

FIG. 6 is a diagram illustrating significant preferential conformations of amino acids for helix, sheet and loop;

FIG. 7 illustrates a table of the Best-Fit-Curve properties of PRIMAL;

FIG. 8 is a tabular representation of experimental results associated with a sequence conversion and finger matrix comparison system according to the present invention;

FIG. 9 is a tabular representation of experimental results associated with altering the order of segments of sequences;

FIG. 12A illustrates an example of separation according to one embodiment of the present invention;

FIG. 12B illustrates an example of separation according to one embodiment of the present invention using logprime function;

FIG. 12C illustrates an example of a finger matrix according to one embodiment of the present invention.

DETAILED DESCRIPTION OF PREFERRED EMBODIMENTS

The present invention will be explained below in the context of an illustrative genetic data processing application. However, it is to be understood that the present invention is not limited to such a particular application. Rather, the invention is more generally applicable to any situation where it is desirable to perform a comparison between a known data set and test data by representing the data to be compared in a special representational form, i.e., finger matrix, wherein the special representational form is based on prime number theory.

Figure 1:
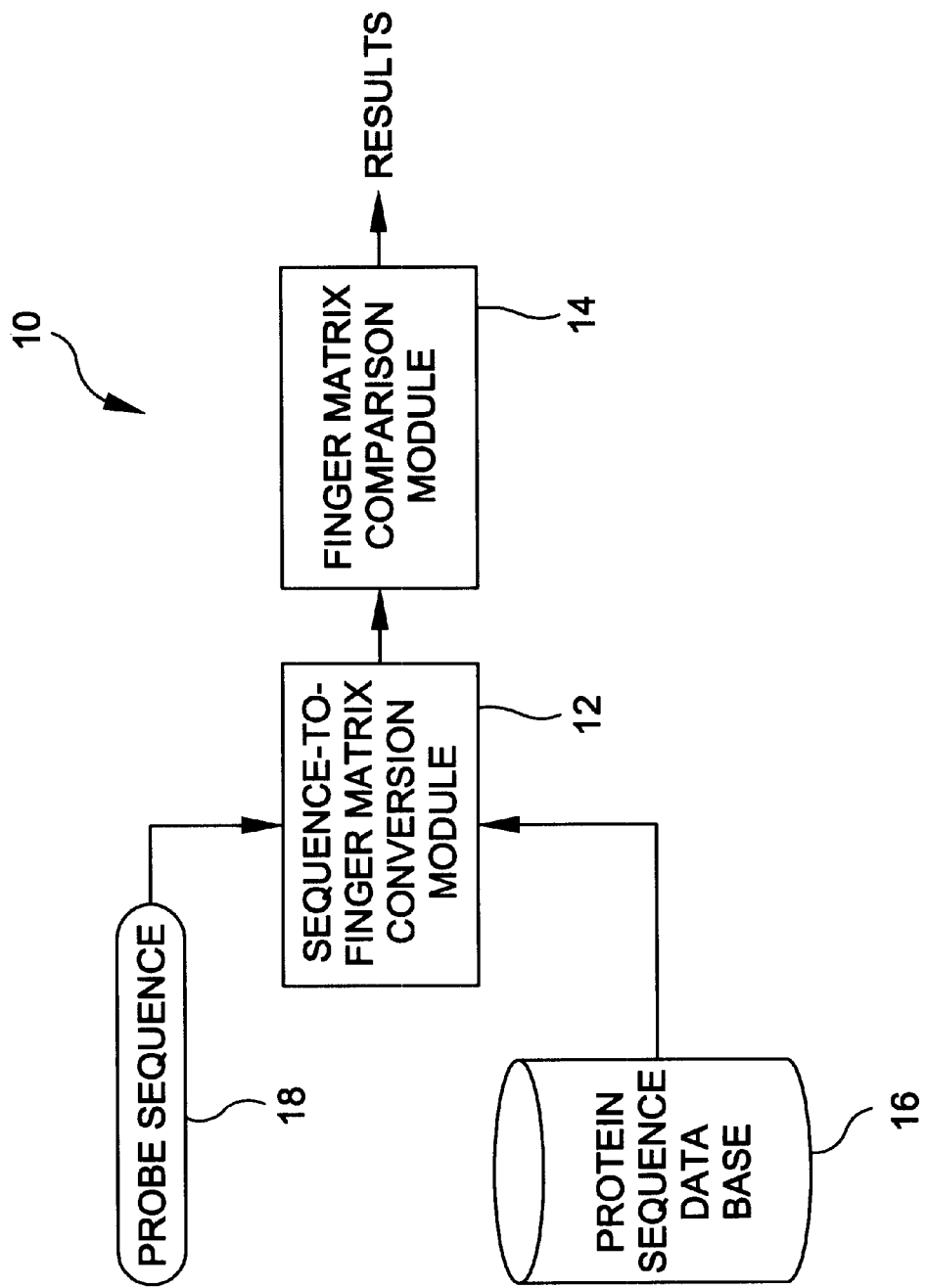
FIG. 1 is a block diagram illustrating a sequence conversion and finger matrix comparison system according to one embodiment of the present invention.

Referring initially to FIG. 1, a block diagram of a system according to an embodiment of the present invention is shown. The illustrative system 10 includes a sequence-to-finger matrix conversion module 12, a finger matrix comparison module 14 and a protein sequence database 16. The system 10 is responsive to a probe (or new) sequence 18 provided by a user. As will be explained in detail below, the conversion module 12 receives the probe sequence 18 and the sequences in the data base 16 and generates respective finger matrices for each sequence. It is to be understood that the data base may be converted prior to receipt of a probe sequence. Also, the data base 16 may be relational or sequential in nature. The finger matrix comparison module 14, as will also be explained, then compares the probe sequence finger matrix to one, more or, preferably, all of the finger matrices representing sequences from the data base and provides resulting difference data for further evaluation by a system user.

It is to be appreciated that the probe sequence may, for example, be provided from the Human Genome Project such that the sequence is submitted to the system in order to generate data representing the comparison of the sequence to one, more or all of the sequences in the known protein sequence data base. The resulting data may have varied applications. For example, it may be used to make a determination as to which sequences in the data base the probe sequence is homologous.

Figure 2:
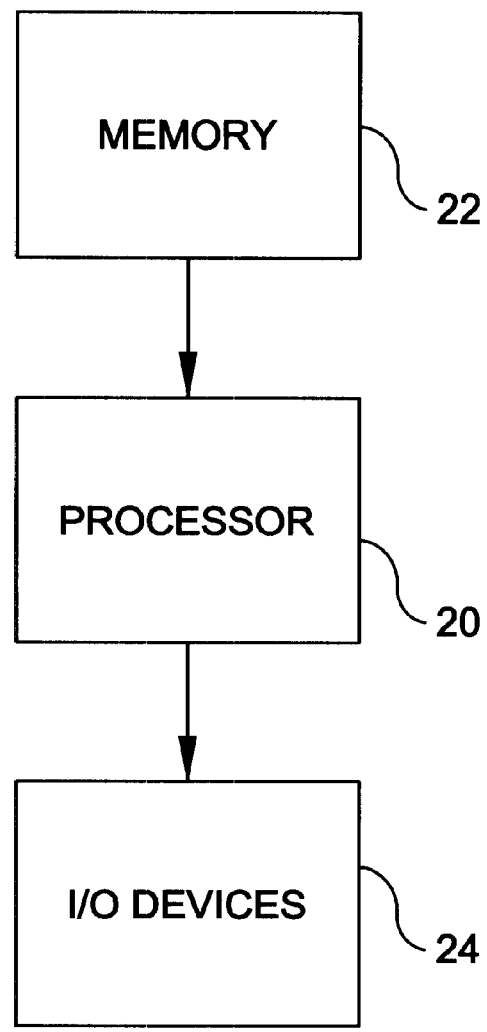
FIG. 2 is a block diagram illustrating a hardware implementation of a sequence conversion and finger matrix comparison system according to one embodiment of the present invention.

FIG. 2 is a block diagram of an exemplary hardware implementation of the system 10 of FIG. 1. As shown, the system 10 may be implemented in accordance with a processor 20, a memory 22 and I/O devices 24. It is to be appreciated that the term "processor" as used herein is intended to include any processing device, such as, for example, one that includes a CPU (central processing unit). The term "memory" as used herein is intended to include memory associated with a processor or CPU, such as, for example, RAM, ROM, a fixed memory device (e.g., hard drive), a removable memory device (e.g., diskette), flash memory, etc. In addition, the term "input/output devices" or "I/O devices" as used herein is intended to include, for example, one or more input devices, e.g., keyboard, for entering sequences and/or other data to the processing unit, and/or one or more output devices, e.g., CRT display and/or printer, for presenting comparison results and/or other results associated with the processing unit. It is also to be understood that the term "processor" may refer to more than one processing device and that various elements associated with a processing device may be shared by other processing devices. Accordingly, software components including instructions or code for performing the methodologies of the invention, as described herein, may be stored in one or more of the associated memory devices (e.g., ROM, fixed or removable memory) and, when ready to be utilized, loaded in part or in whole (e.g., into RAM) and executed by a CPU.

It is to be appreciated that, in an alternative embodiment, the invention may be implemented in a network-based implementation. That is the user may submit a probe sequence at a remote client computer system, while the modules 12 and 14 and data base 16 reside and are executed on a server computer system in communications with the client via a network such as, for example, the Internet. The network could alternatively be a private network and/or a local network. Thus, a user operating remotely on his client computer system, e.g., a personal computer, laptop and/or some other type of personal processing device, enters a probe sequence through application software running on the computer system, e.g., web browsing software and/or a graphical user interface associated with the system. The sequence is passed over the network, in a conventional manner, and processed by server. The server receives the sequence and executes the methodologies of the invention. The server then returns some or all of the results to the client via the network. It is to be understood that the server may include more than one computer system. That is, one or more of the elements in FIG. 1 may reside on and be executed by their own computer system, e.g., with its own processor, memory and I/O devices.

Given a general description of the elements of the protein sequence conversion and comparison system of the invention and various exemplary hardware implementations, the various inventive methodologies will now be explained in detail.

For ease of reference, the remainder of detailed description will be divided into sections as follows: (I) Introduction; (II) Theory; (III) Method; (IV) Results; (V) Modes of Application; (VI) Illustrative Methodologies; and (VII) Extension.

I. Introduction

The present invention is able to overcome the deficiencies of existing methodologies by implementing methods having a fixed length data structure as an alternative representation of protein sequences which is designed to be readily implemented on a relational data base as well as having several other benefits independent of alignment and relational issues. The variable sequence data is compressed into the fixed length data structure by various alternative optional methods described herein.

The general class of method was originally termed SONIC which stands for "Search on Neighbors in Common." A preferred embodiment uses prime numbers for compression in order to carry out an "implicit" or "circumvented" alignment, and is so termed "PRIMAL SONIC FINGER," or "PRIMAL" for brevity. The specific embodiment and related embodiments described is PRIMAL-1. This variant shares the common property of its family members in the SONIC group by representing protein sequences or sets or sub-segments of such to represent protein amino acid sequences ("primary structures") as symbol tables, say 20×20 tables of the 20 types of amino acid residue. Then, each element of the array is one (or optionally very few) numbers in which mathematical code compression methods are use to perform rapid generation and comparison of such representations. The PRIMAL-1 embodiment, discussed here, is distinguished by its use of a simple application of prime numbers. However, the simple method not only illustrates the concept, but was found effective to a level which renders it of immediate utility. As a comparison, a previous intentionally simple "baseline" method SONIC(1), which does not use compression, is given for comparison. Some of these versions are discussed in the Results section below.

The present invention provides that the information of relevance in protein sequences can be reduced to a mathematical abstraction conveniently subject to mathematical rather than string manipulations. As a starting point, information derived from, and more or less characteristic of, protein sequences can be stored in matrices which are 20×20 symbol reference tables. According to the invention, an approach is taken in which a novel formulation of such tables based on use of prime numbers are used solely, explicitly and directly. The matrices are termed "finger matrices," because they represent a "fingerprint" of the sequence under consideration, and particularly because in searches for homologous proteins they serve to finger protein sequences as potentially related to one of interest which is provided as input, without need for alignment. The information stored at each locus relates to the distances along the sequence of neighbors which are the 20 types of symbols in the 20×20 array, up to a cutoff window of k residues (e.g., k=10). Subsequently, direct comparison between the tables, not involving their source sequences, is used to estimate the differences between the sequences of the pilot, ("probe," "query") sequence, and of the remaining data base. This also optionally allows the finger matrices to be pre-computed, off-line, prior to any specific search.

The method of normalization used in accordance with the invention provides a global description of a sequence as a pattern, except in the sense of the use of the window k. The difference between two finger matrices measures differences in that global description. Thus, the role of this method as embodied here is very different to the other approaches, especially TEIRESIAS and SPLASH. It will see two proteins ABC and DBE as significantly different, and even B and ABC as significantly different, since the affect due to A and B is counted. In contrast, however, ABC and BCA will be seen as highly homologous and the measure used. The measure developed correlates well with % (percent) homology by standard means (e.g., CLUSTALW) and thus provides a good estimate of % homology, where homology occurs down the entire sequence. However, it is not significantly affected by "shuffling" the order of segments in one of the sequences.

Several forms of simple finger matrix were first explored to study the balance of information content versus speed, but the common restrictions were that: (a) the elements of the table be a single number (i.e., scalar, not themselves vectors or arrays); and (b) in accord with the above, sequences need not be compared directly or with tables, but the relationship is deduced from comparison of tables alone. Aspect (a) was initially considered only as a starting point, to encourage maximum compression of sequence information, but by a choice of appropriate approach, the use solely of scalar elements of typical precision suffices to meet many of the aspirations of the invention.

The initial comparison of finger matrices was based on an index of similarity, f, which was simply the normalized number of matches of value between two arrays, i.e., each element scored 0 (different separation or zero) or 1 (same non-zero separation distance), and the sum over these values is divided by 20×20. Though this worked well in detecting sequence relations between short sequences, an improvement was developed for sequences of medium and long length.

In accord with this improvement, information is retained about separations other than the closest, without departing from the self-imposed requirement (a) above that the finger array is an array of scalar elements. To pack the requisite information about several separations into scalar quantities with minimal ambiguity, prime numbers are employed. That is, separation distances are converted to prime numbers which when assembled into single quantities retain significant detail about a number of separations within the window. The approach reveals a relationship with prime number arithmetic and pattern recognition for detection of homologies. Notably, it leads to an interesting definition of patterns between data as "prime factors" of non-numeric type, analogous to prime numbers.

A departure is made from mathematical exactness by developing a distance metric between each corresponding element of two finger matrices, rather than testing on identity. The reason is initially pragmatic; this method on average performs significantly better. Clearly in many cases, e.g., if one of the separations is present in one finger matrix and absent in another, it seems quite natural to have this difference contribute to the distance metric. Moreover, as shown, a change of separation to one of similar value makes a smaller contribution to the distance metric, which is intuitive. Many trends which might seem less intuitive are outweighed by the fact that a summation over some 400 elements is performed overall, diluting out less intuitive cases.

Such dilution of less intuitive contributions to the distance metric can be given a self-consistent basis by attention to the choice of statistical hypothesis which is being addressed. In particular, it is not surprising with the extreme nature of the compression of information used that there are some ambiguities in the method of comparison, such that several short distances between residues (say, 2,2,5) might in certain well understood instances return a value close to that for a single long separation (say 8). In considering this, it is important to appreciate the general principle used here that the difference metric is taken as a measure of the evidence for the dissimilarity, not similarity, of two sequences, i.e., that the metric relates to the information for the null hypothesis that the two sequences have no relation. Recalling that finger matrices have only relative meaning and are only utilized in terms of differences between them, then the ambiguous cases naturally imply a down weighting of the measure, which is to say some information is discarded. In other words, the troublesome cases are "damped out."

II. Theory

The following section describes the mathematical theories upon which the methodologies of the invention are based and/or derived.

Prime Number and Pattern Factor Analogy Theorem

An algorithm which seeks to show two data items as homologous by virtue of containing common patterns, independent of the number or order of those patterns, is analogous to an application of the statement of the "fundamental prime number theorem." The patterns are prime factors of pattern or relatively prime in the context of the problem addressed, and their isolation from embedding data corresponds to factorization.

The corresponding proof resides in the axiomatic definition of homology by pattern and the accepted fundamental prime number theorem, as follows.

Homology by Pattern Factor Axiom

If every possible non-empty set $\{p_1 \, p_2 \, p_3 \ldots p_r\}$ of pattern factors $p_1 \, p_2 \, p_3 \ldots p_r$ in a set of data can be expressed as the function $f$ returning value f which maps uniquely and reversibly to that set and to no other set, $$f(p_1 \, p_2 \, p_3 \ldots p_r) = f \leftarrow \rightarrow \{p_1 \, p_2 \, p_3 \ldots p_r\}, r \geq 1 \tag{1}$$

except that set of pattern factors is in this context a disordered set such that the order of the pattern factors is not taken to consideration (does not influence the value $f$), then any two sets or subsets of data A, B with the same value of $f$, $f_A = f_B$ can be said to be homologous by their pattern factors which are thereby $p_1 \, p_2 \, p_3 \ldots P_r$.

Fundamental Prime Number Theorem.

Every natural number n (>1) can be expressed as the product of primes (prime factors) in the form:

$$n = p_1 \, p_2 \, p_3 \ldots p_r, r \geq 1 \tag{2}$$

and there is only one such expression as a product (decomposition into prime factors), if the order of the factors is not taken into consideration. (See Theorem 4 in T. Nagell, "Introduction to Number Theory" John Wiley & Sons, Inc. NY, 1951).

Corollary on Encoding the Component Pattern Factors

If equation (2) holds for all natural numbers, then it also holds for each individual prime $p_1$ and $p_2$ and $p_3 \ldots$ and $p_r$. Thus $f(p_1) = \leftarrow \rightarrow \{p_1\}$, and the individual p are also encodable.

Corollary on Preservation of Information Concerning Multiplicity of Same Patterns Since equation (2) is not confined to unique primers, we can for example encounter $p_1 = p_2$. Two patterns are said to be the same if they are homologous by pattern content, i.e., if $\{p_1\} \leftarrow \rightarrow f_1 = f_2 \leftarrow \rightarrow \{p_2\}$ and $p_1, p_2$ can be replaced by $(p_1)^2$. That is, generally, if there are $n(1)$ occurrences of any of $p_1$ and so on for other primers, then the number of occurrences $n(1), n(2)$ or each pattern is also retained. This conclusion is consistent with Goedel's formulation as follows T. Nagell, "Introduction to Number Theory" John Wiley & Sons, Inc. NY, 1951.

Goedelian Formulation.

A string $S$ can be formulated uniquely (i.e., to a unique Goedel number) as a set of substrings or characters (1), (2), (3), ..., when the substrings can be quantified as integers $i(1), i(2), i(3)$ and successive primes are raised to the power of those integers.

$$S \rightarrow 2^{i(1)} \times 3^{i(2)} \times 5^{i(3)} \times 7^{i(4)} \ldots i(j) \subset S \quad (3)$$

Sufficient Mapping Theorem

Let the values $f$ of $f(p_1 \, p_2 \, p_3 \ldots p_r)$ be $f(p_1 \, p_2 \, p_3 \ldots p_r | a, b)$ conditional upon the specification of the pair of residues, thus corresponding to the entry to be made in the 20×20 finger matrix. By choosing to make reference to no other sequence symbol than a,b, then all metrics based on equations (2) and (3) such as can specify the relation between a and b are distances (separations) along the sequence, or indications of nonoccurrence in the sequence.

An approach relating p to distances over a specified range of distances so as to preserve that information such that it is in principle recoverable from the value of the entry at each element of the finger matrix, is deemed sufficient. Let each p now be a function of the observed separation m between the specified residues a at I and b at i+m, up to and including a maximum value for m, m=k (i.e., a specified separation window k), and occurrence vs. nonoccurrence in the window or sequence. Let such nonoccurrence be indicated by zero. The mapping $f(p) = f \, w\{p\}$ is then here implemented by using for f the function:

$$\Lambda(m) = \log(\mathcal{P}(m)) \leftarrow \rightarrow m, \, \zeta(0) = 0 \quad (4)$$

where $\mathcal{P}(m)$ is the (m)th prime number in the series 2,3,5,7,11,13,17, ..., and log is the natural logarithm taken in part for computational efficiency and also because of its analogy with a probability-like quantity which is a measure of the density of primes (see below). The lowest value case is $\mathcal{P}(1)/1=2$. Note that equation (4) implies an estimate for the reciprocal of the probability (p*) required to locate any prime number in the range 1 ... n. Then $\log(\Lambda(m)) = -\log(p^*)$ is a measure of the information to locate any prime number in the range 1 ... n.

In equation (4) $\log(\mathcal{P}(d)) \leftarrow \rightarrow m$, subject to arithmetic precision, and $\mathcal{P}(m)$ is necessarily prime. Then by equations (1) through (3), the information in a set of m and hence $\mathcal{P}(m)$ can also be recovered from the value of the entry for each element of the finger array (i.e., sufficient mapping is performed, subject to precision), by $f \, f(p_1 \, p_2 \, p_3 \ldots p_r) = f \leftarrow \rightarrow \{p_1 \, p_2 \, p_3 \ldots p_r\}$, $r \geq 1$ where f is the summation function corresponding to equation (5):

$$\Sigma_i \Lambda(m(i)) = \Sigma_i \log(\mathcal{P}(m(i))) \leftarrow \rightarrow \{m(1), m(2), m(3) \ldots\} \quad (5)$$

where $\mathcal{P}(m)$ is the (d)th prime number in the series 2,3,5, 7,11,13,17, ..., and log is the natural logarithm. The values of relevance here are:

| m | $\Lambda$ (m(i)) |
|---|---|
| 1 | 0.6931 |
| 2 | 1.0986 |
| 3 | 1.6094 |
| 4 | 1.9459 |
| 5 | 2.3979 |
| 6 | 2.5649 |
| 7 | 2.8332 |
| 8 | 2.9444 |
| 9 | 3.1355 |
| 10 | 3.3673 |

Note that:

$$\Lambda(m) = \log(\mathcal{P}(m)) = \mathcal{P}(m)/m \geq \log(2) \quad (6)$$

The proof rests on the classic (1') prime number theorem of Hadamard and Poussin (the Gauss conjecture) which states that the number of primes less than natural number n is approximately n divided by the logarithm of n, the approximation diminishing with increasing n. Let n be itself prime, then substitute prime(m) for n, where prime(m) is the mth prime number. The lowest value case is $\mathcal{P}(1)/1=2$. Note that equation (4) implies an estimate for the reciprocal of the probability required to locate any prime number in the range 1 ... n.

$(\Lambda(m))$ may thus also be used as a measure of that information and a sum of several such terms would have the status of an "OR" logical operation applied to those probabilities.

Finger Matrix Symbol Set Theorem

If a set of symbols (e.g., amino acid residue types) is to be treated as a common set (any one member being taken as identical to any other member), then this equivalent in the calculation of the distance metric f between two finger matrices by taking the absolute value only after summation of the finger matrix differences over the set members. That is, if $t(a,b)$ with $t(a,b)=0, 1$ is a symbol membership matrix (e.g., a 20×20 table of amino acids) with elements scored 1 if a and b are in common set and 0 otherwise):

$$f = \left| \sum_{a=1,20}^{20} \sum_{b=1,20}^{20} (1 - t(a, b) + t(a, b) \cdot |F_A(a, b) - F_B(a, b)|) \right| \quad (7)$$

The proof is trivial, resting on the equivalent effect of pooling the data for the symbols before calculating the (reduced size) finger matrix.

Finger Matrix Symbol Fuzzy Set Interpretation

More generally and importantly, if $t(a,b)$ is the symbol transition (e.g., 20×20 "Blosum-like") array for probabilities of transition between symbols (e.g., accepted substitution between amino acid residues) from symbol a to symbol b, then the above equation (7) is also a valid distance metric. The above equation (7) includes the simple case where all symbols (e.g., amino acids) are the sole members of their sets, that is, $t(a,b) = 1$ if $a=b$ and $t(a,b) = 0$ otherwise.

It could be argued that this can only be an interpretation rather than a theorem as it rests on the definition of the distance metric in terms of transition probabilities and of validity in that context, but it is evident that it can readily be shown consistent with the above in the limiting case of $t(a,b) = 0, 1$.

Note that the matrices reflect information in favor of evidence that two sequences are different. Zero value of f can also indicate absence of information, but not information in favor of homology. Certain information, say outside the window of separation, or by virtue of ambiguity inherent in the values of elements F[a,b] is downweighted or discarded.

III. Method

Given the above described theory, the following section describes finger matrix generation and comparison methodologies according to the present invention.

A. Definition of Finger Matrix

The finger matrix is, in the case of amino acid residues of 20 types, a 20×20 array whose elements finger [a,b] are integers representing set {m} of separations m≦k between occurrences of symbols a and b, in the sequence if separation is less than a specified limiting range, and zero otherwise. More specifically, the integer elements of the array correspond to sums of functions of the separations seen for each type of pairs of residues (a,b), e.g., a=alanine with b=histidine, as follows:

$$A[a, b] = \sum_{i}^{L} \sum_{m=i-k>0}^{i-1} \Lambda(m), \forall (a = a_i \& b = b_{i+m}) \quad (8)$$

An example specifying equation (8) in pseudocode is given in FIG. 3. Here m is the specific separations at which the two specified types of residues are found, understanding that m=0 within the summations when (a=$a_i$ and b=$b_{i+m}$) is false, and Λ is the natural logarithm of the mth prime number excluding 1, i.e., defined such that Λ(1)=log(2), Λ(2)=log(3), Λ(3)=log(5), Λ(4)=log(7), Λ(5)=(11) $\quad (9)$ This function is pre-calculated as a look-up table.

We recall from Section II (Theory) that, since the log of the product solely of prime numbers is implied, there is (under the notion of factorization): (i) no ambiguity as to an element F[a,b] comprising e.g., (3×2×2) or (2×6); and (ii) absolute ambiguity about the effective order separations (e.g., because 3×5=5×3), which is required.

B. Scoring of Similarity Between Finger Arrays

In principle, a scoring scheme for comparing two finger matrices could depend only on correspondence or non-correspondence of the values in the elements of the two finger arrays. This would be formally consistent in that the equivalence of the values of the elements implies the equivalence of the set of distances encoded in them. Let {m|A} be the set of separation distances used to specify (assign all the elements of) finger matrix A and {m|A[a,b]} ⊂ {m|A} be the subset of that set of separation distances which is used to specify the value of the element A[a,b] of A, and similarly for finger matrix B. Then (A [a,b]≠ B[a,b]:={m|A[a,b]}≠{m|B[a,b]}) & (A≠B:={m|A}≠{m|B}).

Such a score summed over the matrix would be unambiguous save that it does not reflect which particular elements matched, and which did not. This is acceptable. It would simply indicate, as is normally the case with sequence difference metrics, that many different sequences could lie at the same mutual distance in terms of sequence difference.

However, rather than simply counting the number of equivalent elements between two finger arrays, further information about degrees of difference can be to some extent retained. Whereas simple subtraction between elements F[a, b] introduces a number of problems regarding ambiguity of information about separations of residues where such separations are not identical, it nonetheless provides a net information benefit overall, compared with simply disregarding that information as a non-match. It is true that, for example, three separations of valine and lysine at 1 and 1 and 5 (giving prime numbers 2,2,5) yielding F[a,b]=log(20), is not readily distinguishable from one separation of valine and lysine by 8 (giving prime 19) yielding F[a,b]=log(19). However, since the difference is a small quantity, this merely states that, in effect, we are "discarding" (downweighting) some information for a difference between the two proteins (recalling that f measures evidence in favor of two proteins being different). Further, a set of such coincidences for two related proteins, reflected recurrently and significantly over all 400 elements of the arrays, for two proteins which are actually homologous, is unlikely.

This comparison is achieved by summation over the absolute values of the differences between all corresponding elements.

$$f_{A,B} = \sum_{a,b} |A[a, b] - B[a, b]| / N \quad (10)$$

$$N = \sum_{m=1}^{k} m\Lambda(m) \times 400$$

Note that this is a "penalty measure," that is, it increases with discrepancy between the sequences being indirectly compared, via their finger matrices. An example of pseudocode for comparing a probe finger array (matrix) and a sequence finger array (matrix) is shown in FIG. 4.

C. Quality of Information Retained in the Distance Metric

Despite the above-discussed ambiguities when a distance metric is calculated (equation (9)), and despite the fact that it is naturally downweighted in the counting of evidence in favor of two sequence being different, some useful distance information is nonetheless retained. Clearly, if one term such as Λ(3)=log(5) is missing in one element with respect to its corresponding element in the other finger array, then it appears in the residual which is counted in the final metric. That is, in looking at a difference between two finger matrices, then whenever A contains a set of information that B does not, but B contains no information that A does not, there is some retention of this information in the final score. It is of course ambiguous as to the actual types of residues separated. The trivial proof resides in the notion of moving any one component, e.g., Λ(3)=log(5) of the sum of terms from one element and adding it to that to another element of the same array.

It is worthwhile if the difference metric in cases of non-identity sensibly reflects intuitive notions of degrees of difference. In fact, one reason for the functional form Λ chosen, and its specific use, was to meet the requirement that:

$$\Lambda(m+i)-\Lambda(m) > \Lambda(m+j)-\Lambda(m), \forall (m>k-i), i>j, j \quad (11)$$

That is, a separation implicit in A which differs from that implicit in B, but which is nonetheless still of similar distance, is scored less than one of dissimilar distance. As the method stands, it also correctly reflects the intuition that the difference between sequences receives less weight when the separations in each sequence are large, allowing for the increased chance of insertions/deletions as "fuzzing" the underling biological-evolutionary similarity in larger separations. For example, a small shift along the sequence for close neighbors originally one apart $|\Lambda(1)-\Lambda(2)|1=\log(2/3)$ is weighted more highly than a short shift along the sequence for neighbors far apart, as for $|\Lambda(9)-\Lambda(10)|=\log(23/21)$.

D. Alternative Embodiments

A variety of modifications are possible. It is initially tempting to chose alternative definitions of A such that the implicit value $\Lambda(k)$ (in the present algorithm,$=\log(23)$) is closer in value to the implied value $\Lambda(k+1)$. At present, $\Lambda(k+1)=0$, since the contributions of separations between a and b are not evaluated when lying outside window k. The method of "reverse counting," viz:

$$\Lambda(1)=\log(k),$$

$$\Lambda(2)=\log(k-2),$$

$$\Lambda(k-3)=\log(5),$$

$$\Lambda(k-4)=\log(7),$$

$$\Lambda(k-5)=(11) \quad (12)$$

would seem to give an intuitively tidier finger matrix when looked at from this point of view individually, but in practice, it is only differences between finger arrays which are of interest, so this provides no great advantage. In any event, it is contrary to the intuitive desirable trend discussed in the previous section: with an alternative algorithm with "reverse counting" we would encounter the problem that $|\Lambda(1)-\Lambda(2)|=\log(23/19)$, while $|\Lambda(9)-\Lambda(10)|=\log(2)$, which seems counterintuitive to the above discussed insertion/deletion effects.

A seemingly obvious solution would be to replace each zero element by $\Lambda(k+1)$ which is $\log(29)$ in the case of $k=10$. With $k=10$ and the present algorithm, the worst case of a single difference between two finger matrix elements with one different distance $|\Lambda(1)-\Lambda(10)|=\log(23/2)$ as opposed to the case $|\Lambda(1)-\Lambda(11)||\Lambda(1)-\Lambda(29)|=\log(29/2)$, which is again to be compared with $|\Lambda(1)-\Lambda(9)|=\log(19/2)$. Whereas this is the preferred method, this method does not perform significantly better with the data used here and in fact shows a slight deterioration. This may be due to a non-linearity in the data, i.e., it "resides in the biology." Such a linearity has been detected in that pairs which are less than 10 in separation tend to be in the same secondary structure element, especially helix, and those greater than 10 not so.

Other possible methods include use of expected frequencies of correspondence (e.g., $n(a,b).\Sigma_a n(a)/(n(a).n(b))$, based either on global frequencies $n(a)$, $n(b)$ or those local to the protein. Such methods are of course possible but add to the complexity of the method and lose some information in practice.

For proteins of circa 50% homology, the present proposed method gives average indices $f_{A,B}$ of 3 .6. Higher values would imply a less sensitive detection. Those using reverse counting yield 3.9, and those using a non-zero value for $\Lambda(k+1)$ yield 3.8, which are thus marginally less sensitive. Expectancy and other methods do not generally improve on 3.6, they are no longer a minimalist method and thus serves no advantage in speed over the present class of minimalist method.

E. Simpler Methods as a Comparative Baseline

Amongst the methods explored are methods which do not constitute or were expected to constitute improvements, but which were worthy of note here as providing a baseline or control for comparison. For example, in one series of studies the closest approach only is noted, and enter without modification as the value of the finger matrix (equivalent to redefining $\Lambda(m)=m$). In some studies, the magnitude of difference between the entries was retained, viz:

$$F=\Sigma|A-B|/N \quad (13)$$

where N is the sum overall all elements in the matrix. In other studies, normalization via "local standardization" was tested.

$$F=2\Sigma(|A-B|/A+B)) \quad (14)$$

The most minimal case tested which still has some predictive power is the one chosen as a suitable baseline (a control is desirable since, for short sequences, such methods do sometimes perform surprisingly well). Scoring assumes that all non-zero values are 1, being extremely minimalist in that this is equivalent to using finger matrices which are 0, 1 matrices only.

$$F=\Sigma(A=B\&(A>0))/N \quad (15)$$

Here $N=400$ is the number of elements in A and in B and$=$and $\&$ indicate the numerical equivalent of logical operations formed on each analogous element between A and B such that true$=1$ and false$=0$. That is, if the corresponding elements are equal and non-zero, 1.0 is counted in the summation, otherwise 0.0.

F. Data and Interpretation of Scores ("Calibration")

The sensitivity of the measure and its statistical properties were evaluated and the interpretation protocol was calibrated using actual sequences as well as randomly generated sequences. The lysozymes +$\alpha$-lactalbumins, cytochromes, globins and serine proteases were used for clearly homologous sequences in the range of 35%–100% homology. These were of known three dimensional structure, and hence in that operational sense are "certified" as genuinely homologous. The secondary structure of the sequences was also studied for comparative purposes. There only three symbols H ($\alpha$-helix), E ($\beta$-strand), C (coil, turn, loop) resulting in a 3×3 finger matrix. As might be expected, a 3×3 table carries insufficient information. For example, only at high degrees of homology, detectable by other criteria, does a relation between the primary structure finger matrix reflect a similarity in the secondary structure finger matrix. In contrast, however, the specific pairs and distances reflected in the finger matrix showed (not unexpected) strong correlations with secondary structure states. It suggests that the distance metric used here might well be suitable for detecting weak homologies involving single subdomains or smaller motifs.

In addition to the above sets, the set of more subtle plus non-homologous proteins was used as below. These are typically 0–30% homologous, and in some cases higher homology if this was critically dependent on method due to extensive insertions/deletions. Again, proteins of known three dimensional structure are used and the secondary structure was examined to give an indication of the extent of conformational difference between these structures. FIGS. 5A and 5B illustrate an initial test data base of proteins of known conformation and well-defined secondary structures with which the invention may be implemented.

IV. Results

A. Global Intrinsic Statistical Properties of the Finger Matrices

In calculating a combined or average finger table over many sequences, the distributions of pairs in the matrix contributions p(a,b) has no significant departure (95% confidence level) from the product of their independent probabilities of occurrence p(a)×p(b). Indeed, there is no marked departure for finger matrices of most individual proteins. Analysis of data used in the finger matrices shows that there are nonetheless significant correlation between pairs and different secondary structure preferences, as reflected in FIG. 6. This indicates that they would have predictive capability for secondary structure, and in that sense matrices carry indirectly information about the homology between sequences at the more subtle level of secondary structure, and retain that correlation even when there are very marked changes in residues. For example, even if an M-L interaction was absent in one matrix, other pairs with similar helix-forming propensity are still likely to be retained. Significant preferential conformations of amino acids for helix, sheet and loop are shown in FIG. 6. Numbers indicate major separations m (row residue at i, column residue at i+m) and are specified more than once in a continuous zone only when needed to resolve ambiguity. A region of fine balance between helix (3-4) and sheet (1-2) are shown cross-hashed. Other cases close to fine balance but not specifically indicated are between helix and loop and C-A, A-P, G-A, K-P, H-T, E-N (row-column). The pair I-G are also close to balance between loop and sheet.

B. Correlation Between Distance and Percentage Homology

Plots of finger index f scored as above vs. P=(100−% homology)/100 (i.e., P=1 for 0% homology) showed a distribution around a hyperbolic function of F with respect to P, of the form:

$$f = f_{max}/(1 + P_{F=Fmax/2}/P), 0 = <P = <1 \qquad (16)$$

Where $F_{max}$ is the maximum value of the function F and $P_{F=Fmax/2}$ is the value of P at which the curve has half this maximal value. The results below are for range=10. Results are remarkably insensitive for range choice from range=10 upward, and are similar down to range=5, reflecting the fact that the shortest distance between symbols is stored in the finger matrix. Below 5 the shift of the curve upward is significant and $F_{max}=1$ becomes the largest value for the mean curve when range=1, i.e., only adjacent symbols are considered.

FIG. 7 illustrates a table of the Best-Fit-Curve properties of PRIMAL, which is a methodology that compresses information of multiple separations of a pair of residue types into a single scale quantity, with SONIC(1) which is a methodology, which does not use this compression, and retains only the minimum separation encountered for a pair of residue: parameters of curves fitted to relation between % homology and measure f for SONIC(1) and PRIMAL. High quality fit requires a degree 3–4 polynomial, but curves of f versus (100−% homology) are effectively parabolic, and SONIC(1) gives a form sufficiently close to parabolic y=Ax/(x+B), and PRIMAL sufficiently close to linear y=Ax+B, for most purposes with only circa 3% stress. For PRIMAL, the latter rough linear form with an intercept close to zero is convenient: multiplying f by 65 and subtracting from 100% will give a tolerable indication of homology. SONIC(1) includes parameters of the function $f=f_{max}/(1+P_{F=Fmax/2}/P)$, $0=<P=<1$ fitted to the mean and 90% density contour levels of the scatter plot of F versus % homology. PRIMAL is closer to a linear function with f=grad*(100−% homology) with the upper 90% non-linear below 80% homology, converging to zero.

Noticeable is the fact that the set of supposed non-homologous sequences had the same high index value limit of a F=0.9, but that they extended much further down to scores of 0.65 as opposed to 0.85 for randomized sequences. This may be an indication that there are features of non-randomness in the relation which might include elements of cryptic homology. Since such an interpretation might be too far-reaching, at least when seeking to specify quantified limits, it is safer to operationally define future scores in this region as "possible cryptic homologous elements" by reference to this original calibration data.

The spread of the data makes it impossible to define unambiguous % homology tables with respect to the value of F, but does not prohibit setting up overlapping ranges as in FIG. 8. It can be seen that the range of F=0.35 to F=0.65 is least informative.

C. Sensitivity Tests

The method measures a global effect along a sequence (except in the sense of the use of the cut-off window) and the difference between two finger matrices measures the difference between two sequence. This distinguishes it from methods like TEIRESIAS and SPLASH. If a probe corresponds to a domain B which is in another protein embedded in a longer sequence, say a protein ABC, then when B is identical in both cases, the B will return a zero contribution to f and the f for sequence ABC is the same as that for AC save for "end effects," i.e., the contributions to the finger matrix from pairs spanning the changed boundaries between A and C. The method is not however sensitive to the order of segments, that is, it detects ABC and CBA as highly homologous. FIG. 9 describes some experiments in "shuffling" protein segments. Note that "shuffling" the order does not greatly affect the f measure between two sequences.

V. Modes of Application

The modes of application are exemplified as follows. In each case, one has at least one probe sequence or part thereof which is the "new" protein or sequence of interest, and this is tested against one or more sequences on a data base, or pooled families of proteins or their commonly recurrent parts such as domains. The probes sequence(s) and target sequence(s) are rapidly converted to finger matrices and the matrices compared.

(1) To identify proteins which are from the same or similar family, in a large data base, either by calculating the finger matrix of the sequence each time for comparison with the probe, or by storing a data base of finger matrices. The original single data bases and the finger matrix data bases are about the same order of size, since the normal finger matrix if 400 numbers in length and protein sequences can be 50 up to 1000 or characters, typically 100–500. Also, an initial scan can be performed in a prior study, which for some applications would also be a sufficient study, by searching the finger matrix for a new sequence of interest against a data base consisting only of precalculated finger matrices for sequences. Once finger matrices are searched only against finger matrices, rather than the finger matrices being calculated at the moment of comparison, there are many variations on this theme for faster and related applications which should be evident for anyone skilled in the art of sequence analysis. For example, the pattern features for families of related sequences can be stored in a finger matrix much as described above for a single sequence, allowing a very fast search to be conducted between families rather than individual sequences. For such purpose and for applications (3,4,5) below, families, or families of domains, can be pooled into one generic, representative finger matrix.

(2) To quantify the degree of relation between two sequences of similar lengths which are known or expected to be related.

(3) To compare segments, consensus sequences, domains, blocks and other recurrent themes in protein sequence evolution. For this purpose, finger matrices can also be assembled from more than one protein at a time, notably whole families of proteins or protein domains, so giving a more generally representative matrix. Conversely, short segments of sequences such as consensus sequences or "seqlets," can also be re-expressed as finger matrices and used in searches.

(4) Alternatively, finger matrices allowing for variations of amino acids commonly seen in related sequences can be generated but from one protein sequences by pooling of classes or use of reduced matrices, as suggested by equation (7) above and the paragraph "Finger Matrix Fuzzy Set Interpretation" which follows it. This method is not identical to that of application (3) above, but the differences resulting are also of scientific interest. Related to this is the fact that finger matrices of pooled families can be compared with matrices developed by pooling amino acid residues of common type (equation (7)) to see the extent to which substitution in evolution in the family follows that description of common type. This is analogous to saying "are the substitutions conservative?" However the definition of conservative is a complex issue. In reality, conservation varies with closely related protein, protein families, protein superfamilies, or all data pooled.

(5) In the preferred application, one may construct such a computer data base of segments and domains which recur in nature, albeit with extensive amino acid sequence variations, and to use these in a scan against protein sequences. The data base may contain finger arrays of pooled sequences, or "fuzzy states" as discussed above and in relation to equation (7). Such a scan need not be exhaustive ("fine") down the probe or "new" sequence, say from residue 1 to 50, 2 to 51, 3 to 51 but at much longer ("course") intervals, say 1 to 50, 10 to 60, 20 to 70, . . . depending on the sensitivity required. Related domains which have scores of 0.5 suggesting significant homology will still show values significantly above zero when displaced sideways some 20% into non-homologous regions. Once a signal above 0.5 is detected, or lower if very subtle matches are of potential interest, then the local region can be scanned more finely. Though this method is "preferred," its purposes are slightly different to those of application (1) and other applications, depending on the scientific emphasis. For example, the present method (3) will be valuable in detecting weak relationships between evolutionarily distant proteins with some related parts, determining protein function by identification of functional domains, and in modeling of three dimensional structures when some of the matches sequences are of known experimental three dimensional structure.

VI. Illustrative Methodologies

Figure 10:
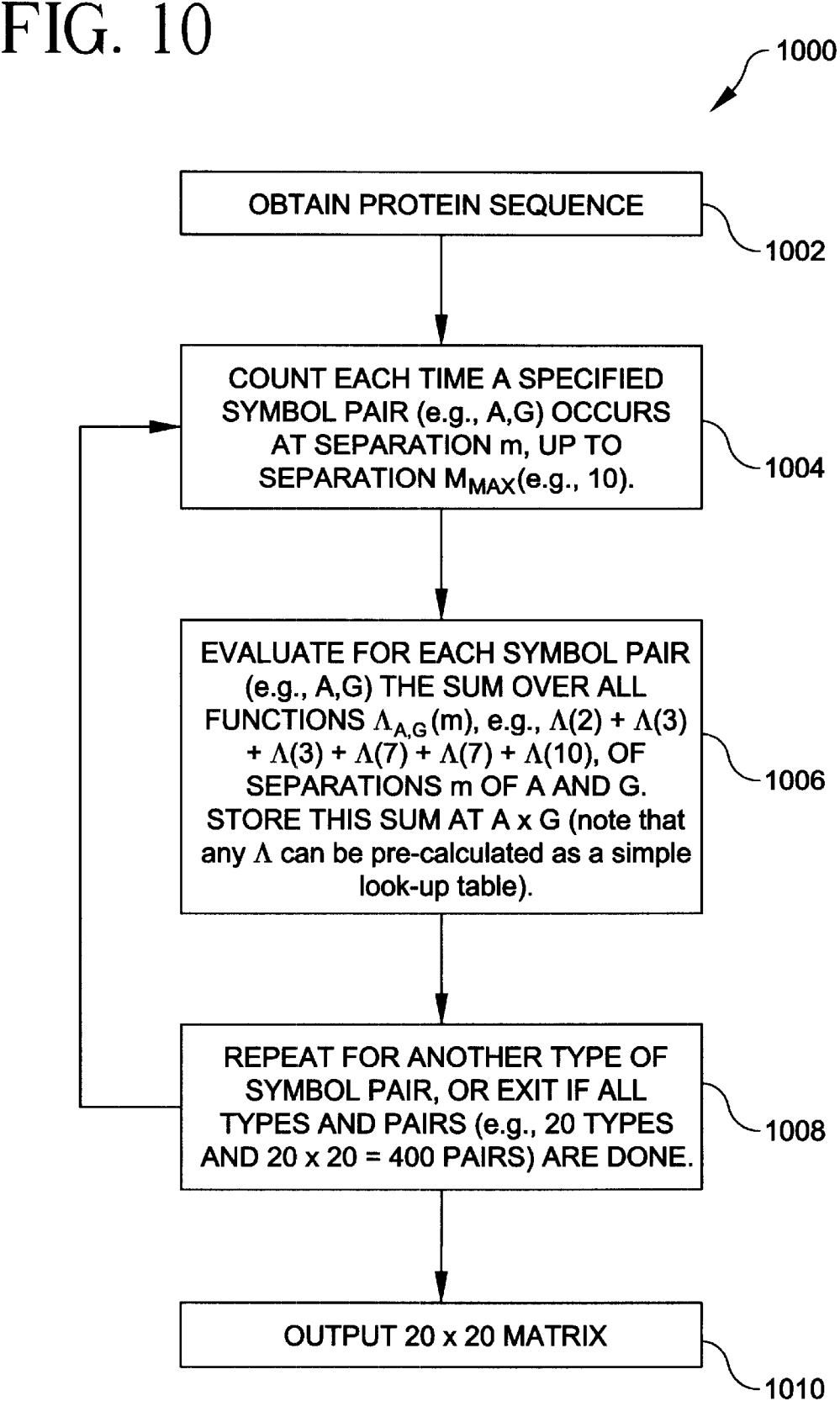
FIG. 10 is a flow diagram illustrating a sequence-to-finger matrix conversion process according to one embodiment of the present invention.
Figure 11:
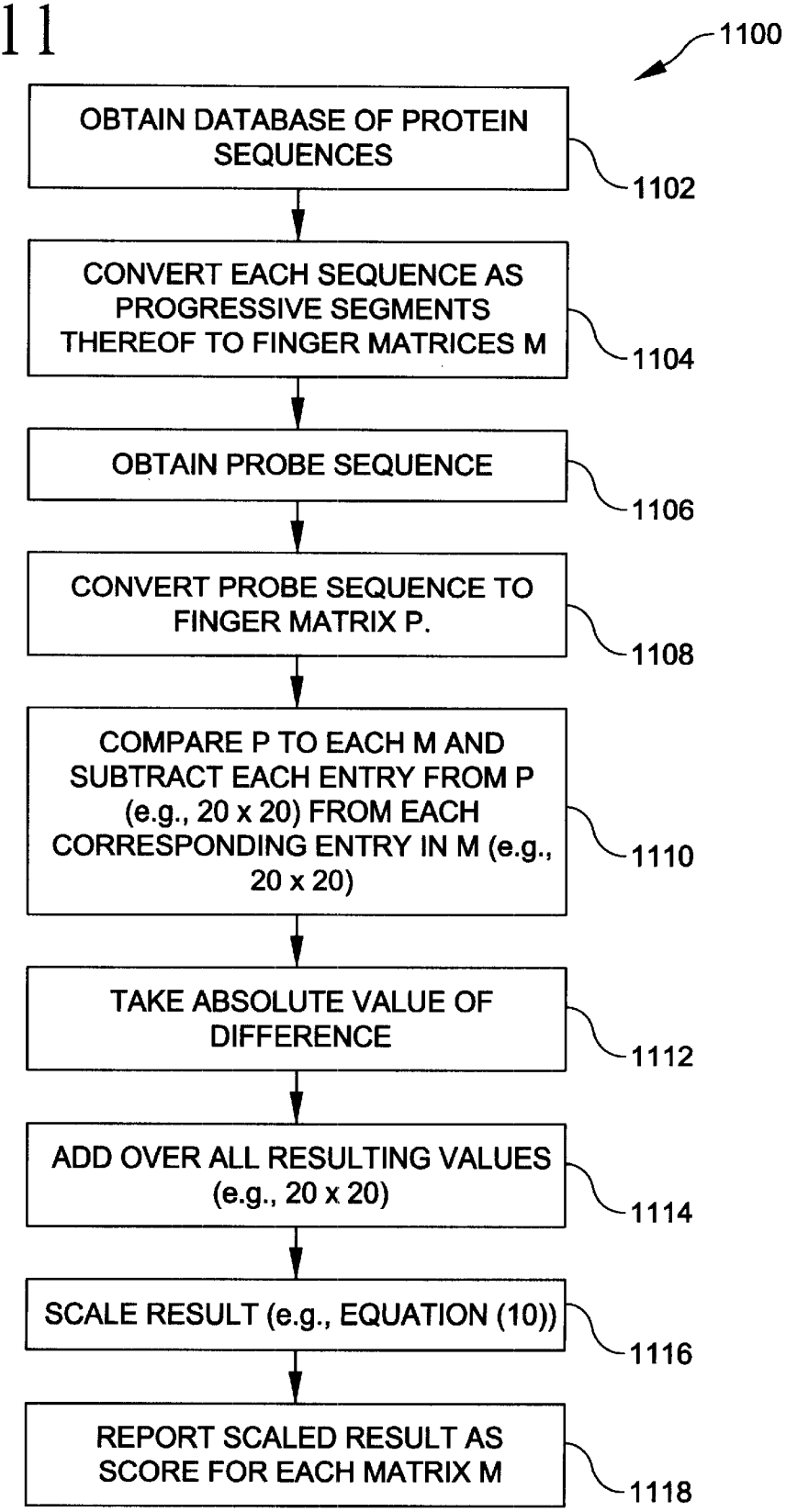
FIG. 11 is a flow diagram illustrating a finger matrix comparison process according to one embodiment of the present invention.

Given the above detailed description explaining the theories and methodologies associated with the invention, FIGS. 10 and 11 depict illustrative finger matrix (array) computation and comparison processes, respectively, in order to summarize the steps presented above.

Referring now to FIG. 10, a sequence-to-finger matrix conversion process 1000 is shown. It is to be appreciated that this is the process that the module 12 (FIG. 1) performs in the system 10. Since this is the same process that is applied to all sequences, i.e., both the probe sequence 18 and the sequences from data base 16, the general term "protein sequence" is used. In step 1002, a protein sequence is obtained. In step 1004, we count each time a specified symbol pair (e.g., A, G) occurs at separation m, up to a pre-specified separation $m_{MAX}$ (e.g., 10). In step 1006, each symbol pair (e.g., A, G) is evaluated by generating the sum over all functions $\Lambda_{A,G}$ (m), eg., $\Lambda(2)+\Lambda(3)+\Lambda(3)+\Lambda(7)+\zeta$ (7)+$\Lambda$(10), of separations m of A and G. This sum is stored at A×G (not same as G×A). Note that any A can be pre-calculated as a simple look-up table. In step 1008, steps 1004 and 1006 are repeated for another type of symbol pair. Once all types and pairs are done, e.g., 20 types and 20×20=400 pairs, the 20×20 finger matrix is output.

Referring now to FIG. 11, a finger matrix comparison process 1100 is shown. It is to be appreciated that this is the process that the module 14 (FIG. 1) performs in the system 10. In steps 1102 through 1108, finger matrix p for the probe sequence and finger matrices M are respectively generated for each sequence in accordance with the process of FIG. 10. As mentioned above, the data base sequences may be converted to finger matrices in advance and stored in a data base of finger matrices. This data base may be relational or sequential in nature. In step 1110, p is compared to each M wherein each entry from p (e.g., 20×20) is subtracted from each corresponding entry in M (e.g., 20×20). In step 1112, the absolute value of each difference is taken. In step 1114, all resulting values of the comparisons (e.g., 20×20) are added. The result may be scaled in step 1116 in accordance with equation (10). Then, in step 118, the scaled result is reported as the score for each matrix M. The user can then do as he wishes with the information. Each score gives the user information as to the homology between the probe and the corresponding sequence from the data base used to generate the score.

By way of simple example, consider the following. If residue types ("symbols") R and S occur one apart, add in the function for that (i.e., log 2), if 2 apart add in the function t for that (i.e., log 3), and if both occur, add the function of 1 to that of 2, and write that sum in the matrix element for that protein (i.e., log 2+log 3). For sequence of two symbols RSRRR, where RS occurs once, SR occurs once, RR occurs twice, RXR occurs twice, RXXR occurs once, RXXXR occurs once (X referring to a wildcard position, that is, can be an R ore S), separation may be represented as shown in FIG. 12A. Using the logprime function (starting primes at 2), the separation may then be represented as shown in FIG. 12B. The finger matrix for a protein, say X, is thus represented as shown in FIG. 12C.

The difference between two such matrices for two proteins X,Y, i.e., the corresponding terms of two matrices, is what is of interest and this part of the calculation of course stays the same whatever the window. The measure of difference between the two matrices is done by taking each element of matrix X minus that of matrix Y, the absolute values of such differences being added up over the four RS SR SS SR difference elements and then "normalized" in some manner. That is, calculate: abs[X(RR)−Y(RR]+abs[X(RS)−Y(RS)]+abs[X(SS)−Y(SS)]+abs [X(SR)−Y(SR)] and "normalize" it as described. If the sequences X and Y (and so the X and Y matrices) are the same, the difference is of course zero, whatever the normalization. So "normalization" is a question of "scaling."

VII. Extension

Whereas the method as described above works best for sequence of similar length, in so much that an extra section in one compared sequence is a difference in pattern content, the method is not confined to rapid identification of more closely related proteins which are typically of similar length. Nor is extension of the method to the case of proteins differing greatly in length dependent on a scan of portions of one sequence with respect to each other. A more fundamental method of comparison rests on the fact that comparison can be made with several different proteins or segments of proteins at the same time, so as to deliver a single comparison score which might, for example, show that a protein of interest is related to two or more specific proteins.

Applications of the above type are possible because the finger arrays are approximately additive, such that a protein sequence which can be considered as composed of two parts say AB can be compared with two smaller proteins or fragments of sequence separately. That is, the operations of subtraction are performed more than once, and the absolute value of the difference for each element are performed when the operations are completed. In the method described above, the matrix F[A-B] which represents the matrix of elements of the absolute value of the difference of each element taken between a probe sequence A and test sequence B on a data base might be defined by the matrix operation F[A-B]=F[A]- F[B]. In this use, the operation of subtraction also indicates that the absolute value of the difference of the two corresponding elements is taken. That is, the result is counted positive irrespective of it being positive or negative. In the same notation, the difference between probe sequence A and two proteins or protein fragments B and C might be represented by F[A-B-C]=F[A]- F[B]- F[C]. This process can be defined in the following section of program in the C or C++ computing language in which the finger matrix for probe protein A is represented by array p and the finger matrices for two proteins B and C are represented by finger[f1] and finger[f2] respectively.

```
score=0;
for (a=1;a<=20;a++)
  {
  for (b=1;b<=20;b++)
    {
    p=probe[a][b];
    f1=finger[p1][a][b];
    f2=finger[p2][a][b];
  score +=abs(p-f1-f2);
    }
  }
print "Score=", score/total, "\n";
```

The validity of this approach can be clearly shown for the case F[A-B-C]=f[A]-F[B]-F[C] where B=C by preparing a dimer sequence A, which is the same sequence extended once by a copy of itself. The above theoretical considerations would predict that the score for f[A-B-C] would be close to zero in such a case. The table of final scores is represented by:

| | target = 4APE1E | target = 4APE1E dimer | target = 2APP1E |
|---|---|---|---|
| probe = F[4APE1Edimer] −F[target] | 0.825 | 0.000 | 0.998 |
| probe = F[4APE1E dimer] −F[target]−F[target] | 0.017 | 1.633 | 0.743 |

Here 4APE1E is an endopthiapepsin and 2APP1E is a pencillinopepsin. which are acid proteases and weakly related.

Note that a low score of 0.017 is obtained if F[B] is subtracted twice, reflecting the fact that two copies of sequence B are found in the probe protein sequence dimer A. The value is not exactly zero because new pattern components appear in the region where the two sequence copies are spliced together. Note that these proteins prior to the above artificial doubling in length already naturally consist of two weakly related domains. The first half and second half of 4APE1E relate to each other with a score of 0.276 and the first half also relates to the first and second halves of 2APP1E of corresponding same length with scores of 0.219 and 0.2843 respectively.

The invention is flexible and a variety of modes of method and application are possible. For example, this can be readily extended to simultaneous comparison with more than two proteins or protein fragments by generalizing to F [A-B-C-D- . . . ]- F[A]-F[B]-F[C]-F[D]- . . . , and so on indefinitely, by introducing further arrays finger[p3][ ][], finger[p4][ ][]and so on. The general problem is to find the solution of the coefficients F[A-B-C-D- . . . ]-$C_A$.F[A]-$C_B$F [B]-$C_C$F[C]-$C_D$F[D]- . . . which can be determined by optimization or by successive testing of each test protein or protein segments, especially when commonly recurring segments frequently found in proteins are stored on a data base and used as the database (source of the F[B], F[C], F[D], . . . , which can also be pre-calculated and stored on the data base) for the comparison with the probe.

A preferred embodiment finds coefficients for matching known recurrent protein fragments, also called 'domains,' 'sub-domains' or 'blocks', such as are presented in the Expasy BLOCKS of Henikoff et al. at the FHCRC in Seattle (USA) data base as described on the ExPASy web page http://www.expasy.ch/cgi-bin/prosite-search-ful as of 1999. However, in the present application, finger matrices are employed, rather than regular expressions such as [LIVMFGAC]-[LIVMTADN]-[LIVFSA]-D-[ST]-G-[STAV]-[STAPDENQ]-x-[LIVMFSTNC]-x-[LIVMFGTA] (which correspond to the acid protease group containing endothiapepsins used in examples above). Note that finger matrices for pooled amino acid types, say large hydrophobic, can also be represented as described above. Ideally, the coefficients $C_A$, etc., would be low if the block does not occur in the protein of interest, and approximate N if the same block occurs N times in the probe protein. However, this presumes that there are no correlations between the blocks and a high degree of match with the probe. Since blocks may not be independent, have significant matches between themselves, then more typically two blocks might match with a score of approximately 0–4–0.5. Various methods can be envisaged by which the data for the protein segments on a standard data base of fragments might be initially sorted, clustered, ranked or otherwise arranged to make efficient the comparison with a probe protein, so that when a match is found, the probe is directed towards other protein for which a match might reasonably be expected. Alternatively, clearer results in an initial scan might be obtained for identification with parts of a probe protein if protein segments which have too high a correlation with each other are avoided.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. Apparatus for characterizing an item described by an ordered string of characters, the apparatus comprising:
at least one processor operative to: (i) for a set of separation metrics each representing a unique number of positions of separation between arbitrary characters in a character group in the ordered string of characters, associating first data with each separation metric; generate a set of character groups, wherein each character group comprises at least two characters contained within the ordered string of characters; and (ii) for at least one given character group in the set of character groups, for each given separation metric in the set of separation metrics, generate second data representing a number of occurrences that the given character group satisfies the given separation metric; generate compressed third data associated with the given character group, wherein the third data is based upon the second data and the first data, wherein said third data corresponds to the characterization of said item; and memory, coupled to the at least one processor, which stores at least a portion of results associated with one or more of the operations performed by the at least one processor.

2. An article of manufacture for generating data characterizing an item described by an ordered string of characters, comprising a machine readable medium containing one or more programs which when executed implement the steps of:

for a set of separation metrics each representing a unique number of positions of separation between arbitrary characters in a character group in the ordered string of characters, associating first data with each separation metric;

generating a set of character groups, wherein each character group comprises at least two characters contained within the ordered string of characters;

for at least one given character group in the set of character groups, for each given separation metric in the set of separation metrics, generating second data representing a number of occurrences that the given character group satisfies the given separation metric;

generating compressed third data associated with the given character group, wherein the third data is based upon the second data and the first data; and storing the third data for subsequent use.

3. The apparatus of claim 1, wherein said item is a protein sequence, and each character in the ordered string of characters represents at least one amino acid.

4. The apparatus of claim 1, wherein each character group comprises a character pair contained within the ordered string of characters, and wherein each separation metric represents a unique number of positions of separation between arbitrary characters in a character pair in the ordered string of characters.

5. The apparatus of claim 4, wherein the third data is stored in an entry associated with the given character pair, wherein the entry is part of a table of entries, wherein each entry corresponds to a unique character pair.

6. The apparatus of claim 1, wherein the first data comprises a set of unique prime numbers corresponding to the set of separation metrics.

7. The apparatus of claim 6, wherein the set of unique prime numbers is an ordered set beginning with the number 2.

8. The apparatus of claim 7, wherein the step of generating the third data associated with the given character pair is generated by:

for each given separation metric in the set of separation metrics, transforming the second data using a function based upon the unique prime number associated with the given separation metric; and adding the transformed second data to a running sum associated with the given character pair.

9. The apparatus of claim 8, wherein the transforming step comprises multiplying the second data by the natural logarithm of the unique prime number associated with the given separation metric.

10. The apparatus of claim 5, wherein the table entries for a given item are compared with the table entries for another item to provide a measure of similarity between the two items.

11. The apparatus of claim 10, wherein comparison between table entries for the two items is based upon the numerical difference between corresponding table entries.

12. The apparatus of claim 11, wherein the measure of similarity between the two items is computed by:

summing the absolute value of the numerical difference between corresponding table entries, and normalizing the resultant sum.

13. The article of claim 2, wherein said item is a protein sequence, and each character in the ordered string of characters represents at least one amino acid.

14. The article of claim 2, wherein each character group comprises a character pair contained within the ordered string of characters, and wherein each separation metric represents a unique number of positions of separation between arbitrary characters in a character pair in the ordered string of characters.

15. The article of claim 14, wherein the third data is stored in an entry associated with the given character pair, wherein the entry is part of a table of entries, wherein each entry corresponds to a unique character pair.

16. The article of claim 2, wherein the first data comprises a set of unique prime numbers corresponding to the set of separation metrics.

17. The article of claim 16, wherein the set of unique prime numbers is an ordered set beginning with the number 2.

18. The article of claim 17, wherein the step of generating the third data associated with the given character pair is generated by:

for each given separation metric in the set of separation metrics, transforming the second data using a function based upon the unique prime number associated with the given separation metric; and adding the transformed second data to a running sum associated with the given character pair.

19. The article of claim 18, wherein the transforming step comprises multiplying the second data by the natural logarithm of the unique prime number associated with the given separation metric.

20. The article of claim 15, wherein the table entries for a given item are compared with the table entries for another item to provide a measure of similarity between the two items.

21. The article of claim 20, wherein comparison between table entries for the two items is based upon the numerical difference between corresponding table entries.

22. The article of claim 21, wherein the measure of similarity between the two items is computed by:

summing the absolute value of the numerical difference between corresponding table entries, and normalizing the resultant sum.

\* \* \* \* \*